United States Patent
Lee et al.

(10) Patent No.: US 9,096,623 B1
(45) Date of Patent: Aug. 4, 2015

(54) METHOD FOR PREPARING RADIOTRACER PRECURSOR SNADAM

(71) Applicant: ATOMIC ENERGY COUNCIL—INSTITUTE OF NUCLEAR ENERGY RESEARCH, Taoyuan County (TW)

(72) Inventors: Ching-Yun Lee, Taoyuan County (TW); Yu Chang, Taoyuan County (TW); Cheng-Fang Hsu, Taoyuan County (TW); Yueh-Feng Deng, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 0 days.

(21) Appl. No.: 14/272,676

(22) Filed: May 8, 2014

(51) Int. Cl.
C07F 7/22 (2006.01)

(52) U.S. Cl.
CPC .................................... C07F 7/2212 (2013.01)

(58) Field of Classification Search
CPC ..................................................... C07F 7/2212
USPC .......................................................... 556/87
See application file for complete search history.

(56) References Cited

FOREIGN PATENT DOCUMENTS

CN          1286843 C   * 11/2006

OTHER PUBLICATIONS

Acton et al., The Jurnal of Nuclear Medicine, vol. 42, No. 10, pp. 1556-1562 (2001).*
Huang et al., Nuclear Medicine and Biology, vol. 29, pp. 741-751 (2002).*
Oya et al., Nuclear Medicine and Biology, vol. 27, pp. 249-254 (2000).*

* cited by examiner

Primary Examiner — Porfirio Nazario Gonzalez
(74) Attorney, Agent, or Firm — Rosenberg, Klein & Lee

(57) ABSTRACT

A method for preparing a radiotracer precursor SnADAM is revealed. The method overcomes shortcomings of conventional synthesis methods including lower yield rate and time-consuming. Moreover, Pd/C catalyst and hydrogen gas are used to catalyze reduction reaction for avoiding the generation of a large amount of intermediate products with similar structures. Thus there is no need to perform isolation and purification processes. The yield rate of the intermediate products is also increased so that its impact on the low yield rate of the final product SnADAM is minimized. A part of the reaction is significantly accelerated by using tris(dibenzylideneacetone)-dipalladium(0) ($Pd_2(dba)_3$) as a catalyst. Thus the production time of SnADAM is shortened.

6 Claims, 4 Drawing Sheets

(2)

(3)

(3A)

(4)

METHOD FOR PREPARING RADIOTRACER PRECURSOR SNADAM

FIELD OF THE INVENTION

The present invention relates to a method for preparing a radiotracer precursor, especially to a method for preparing [2-((2-Amino-4-tri-n-butyltinphenyl)thio)benzyl]-dimethylamine (hereinafter called SnADAM), which is a precursor for $^{123}$I-ADAM, which is an imaging agent for serotonin transporter.

BACKGROUND OF THE INVENTION

A recent theory indicated that the cause of bipolar disorder related to abnormal serotonin chemistry in the brain. Imaging of serotonin transporters is of great value in studies of correlation between changes of the serotonergic system and other mental disorders, and in evaluation of the effects of the antidepressants and monitoring the progress. In order to improve the quality of diagnosis and treatment of individuals with mental disorders, the radiotracer for imaging serotonin transporter has a great potential in clinical use.

Hank Kung, PhD, professor at the University of Pennsylvania has dedicated to develop new serotonin transporter imaging agents and ever mentioned a potential serotonin transporter imaging agent-ADAM in following two papers-"2-((2-((dimethylamino)methyl)phenyl)thio)-5-iodophenylamine (ADAM): an improved serotonin transporter ligand" *Nucl. Med. Biol.* 2000, 27, 249-254 and "Quantification of Serotonin Transporters in Nonhuman Primates Using [123I] ADAM and SPECT", *J. Nucl. Med.* 2001, 42, 1556-1562. According to his studies, it has been proved that ADAM has a potential in clinical applications.

However, there are still technical bottlenecks during the synthesis process of ADAM. Refer to FIG. 1, during the synthesis process of N,N-dimethyl-2-[(4-bromo-2-nitrophenyl)thio]-dimethylamine (compound 4), nitro groups and amides of the reactant N,N-Dimethyl-2[(4-bromo-2-nitrophenyl)thio]-benzamide (compound 2) are reduced into amino groups. The problem of low yield rate often occurs. This is due to water molecule generated during reduction of the nitro group into the amino group. Sometimes the anhydrous-form blue-colored cobaltous chloride ($CoCl_2$) is unable to remove all water molecules in the synthesis system and this causes incomplete reduction of the nitro group. On the other hand, water molecule may react with borane ($BH_3$) so that the reduction efficiency is decreased. Thus the reduction efficiency of the amide is further affected.

Even using 10 equivalents of borane and adding 1.5 equivalents of anhydrous cobalt chloride, not all nitro groups and amides are reduced easily and completely. A mixture of compound 2, compound 3, compound 3A and compound 4 shown in FIG. 2D in different ratios is obtained. The adds complexity and inconvenience in isolation of purification of the compounds. Although Dr. Kung did not add cobalt chloride in this step, the side reactions along with the nitro groups being reduced into the amino groups are still not avoided. After purification, the yield rate of compound 3A produced by the Dr. Kung's method is 80%. This affects the yield rate of the final product SnADAM.

Moreover, during the synthesis of ADAM, the substitution reaction between the compound 4 and bis(tri-n-butyltin) is catalyzed by a zero-valent palladium complex-Tetrakis(triphenylphosphine)palladium($Pd[P(C_6H_5)_3]_4$). The reaction is refluxed for 96 hours to get the final product SnADAM (compound 5). For improvement in synthesis processes to achieve industrialization, the production time should be shortened significantly.

Thus there is room for improvement and a need to provide a novel synthesis method for rapid and high-yield production of radiotracer precursor SnADAM.

SUMMARY

Therefore it is a primary object of the present invention to provide a method for preparing a radiotracer precursor SnADAM in which Pd/C catalyst and hydrogen gas are used simultaneously for catalysis and reduction of N,N-Dimethyl-2[(4-bromo-2-nitrophenyl)thio]-benzamide (compound 2) respectively to produce [2-((2-amino-4-bromo-phenyl)thio) benzyl]dimethylacetamide (compound 3), without special purification processes. Then an amide carbonyl group of the compound 3 is reduced by borane. After following acid and alkali treatment, isolation and purification processes, N,N-dimethyl-2-[(4-bromo-2-nitrophenyl)thio]-dimethylamine (compound 4) is obtained. The yield rate of the compound 4 is stable and around 90%, which is significantly higher than the maximum yield rate of about 50% of conventional techniques. Thus the yield rate of the final product SnADAM is improved effectively.

It is another object of the present invention to provide a method for preparing a radiotracer precursor SnADAM in which a new zero-valent palladium catalyst-tris(dibenzylideneacetone)dipalladium(0) ($Pd_2(dba)_3$) is used in combination with triethylamine (TEA) and a nitrogen gas balloon so as to shorten the reaction/reflux time into 48 hours. That means related processes have been finished within half of the time. The SnADAM is produced more efficiently.

It is a further object of the present invention to provide a method for preparing a radiotracer precursor SnADAM in which sodium methoxide (MeONa) is added directly to enhance reaction efficiency of thiosalicylic acid with 2,5-dibromonitrobenzene. The production efficiency of 2-[(4-bromo-2-nitrophenyl)thio]benzoic acid (compound 1) obtained is improved. Thus the efficiency of the whole reaction is also increased.

In order to achieve the above objects, a method for preparing a radiotracer precursor SnADAM of the present invention includes following steps. First, 2-[(4-bromo-2-nitrophenyl) thio]benzoic acid is activated by thionyl chloride ($SOCl_2$) and reacted with dimethylamine to carry out an amidation reaction for production of N,N-Dimethyl-2-[(4-bromo-2-nitrophenyl)-thio]-benzamide. Then catalyze and reduce N,N-Dimethyl-2-[(4-bromo-2-nitrophenyl)thio]-benzamide by using palladium carbon catalyst and hydrogen gas to produce [2-((2-amino-4-bromo-phenyl)thio)benzyl]dimethylacetamide. Next, reduce [2-((2-amino-4-bromo-phenyl)thio)benzyl]dimethylacetamide by borane to produce N,N-dimethyl-2[(4-bromo-2-nitrophenyl)thio]-dimethylamine. Add bis(tri-n-butyltin) into N,N-dimethyl-2-[(4-bromo-2-nitrophenyl) thio]-dimethylamine for carrying out substitution reaction and using tris(dibenzylideneacetone)-dipalladium(0) as a catalyst so as to produce [2-((2-Amino-4-tri-n-butyltinphenyl)-thio)benzyl]-dimethylamine which is a radiotracer precursor. Thus SnADAM, the precursor of the radiotracer for imaging of serotonin transporter, can be produced at a fast rate and in a large quantity according to the steps mentioned above.

BRIEF DESCRIPTION OF THE DRAWINGS

The structure and the technical means adopted by the present invention to achieve the above and other objects can

DETAILED DESCRIPTION

Please refer to following embodiments for details, features and effects of the present invention.

Figure 1:
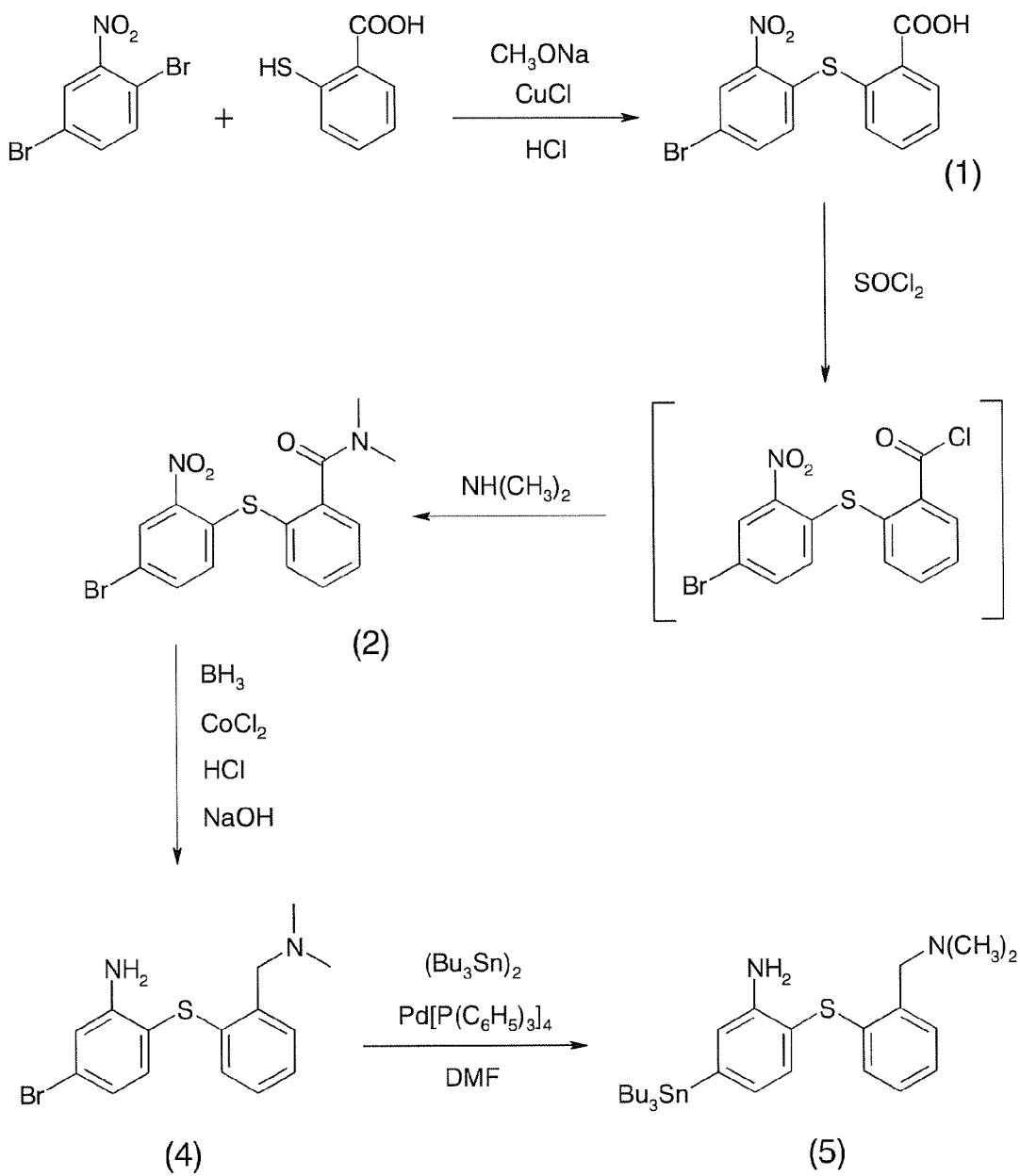
FIG. 1 shows chemical reactions for synthesis of SnADAM in prior arts.
Figure 2A:
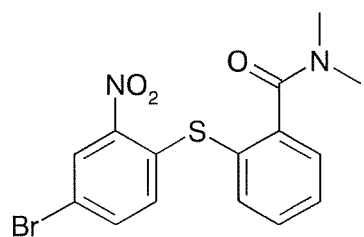
FIG. 2A to 2D show structure of products generated due to incomplete reduction in prior arts.
Figure 2B:
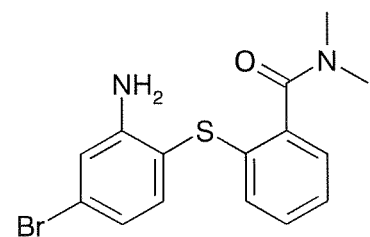
Figure 2C:
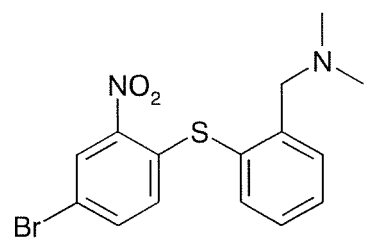
Figure 2D:
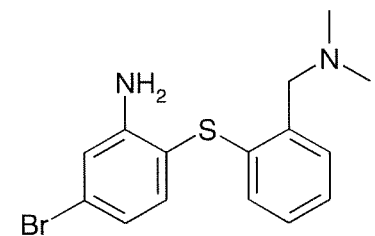
Figure 3:
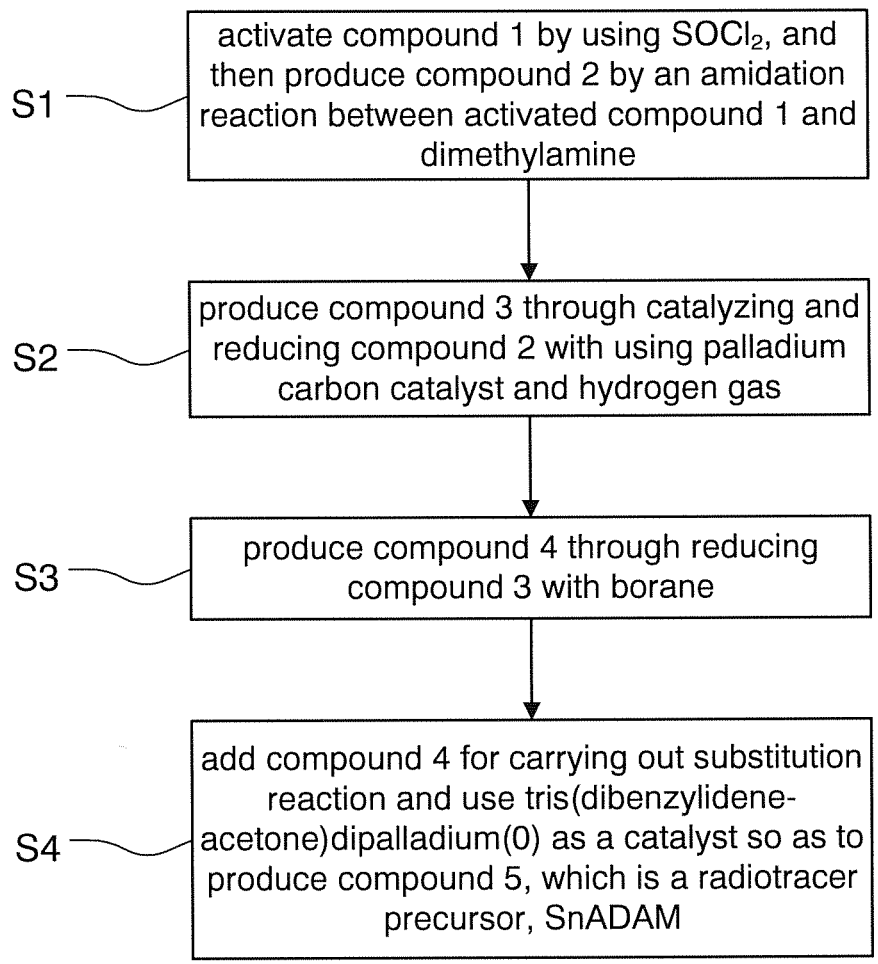
FIG. 3 is a flow chart showing steps of an embodiment according to the present invention.
Figure 4:
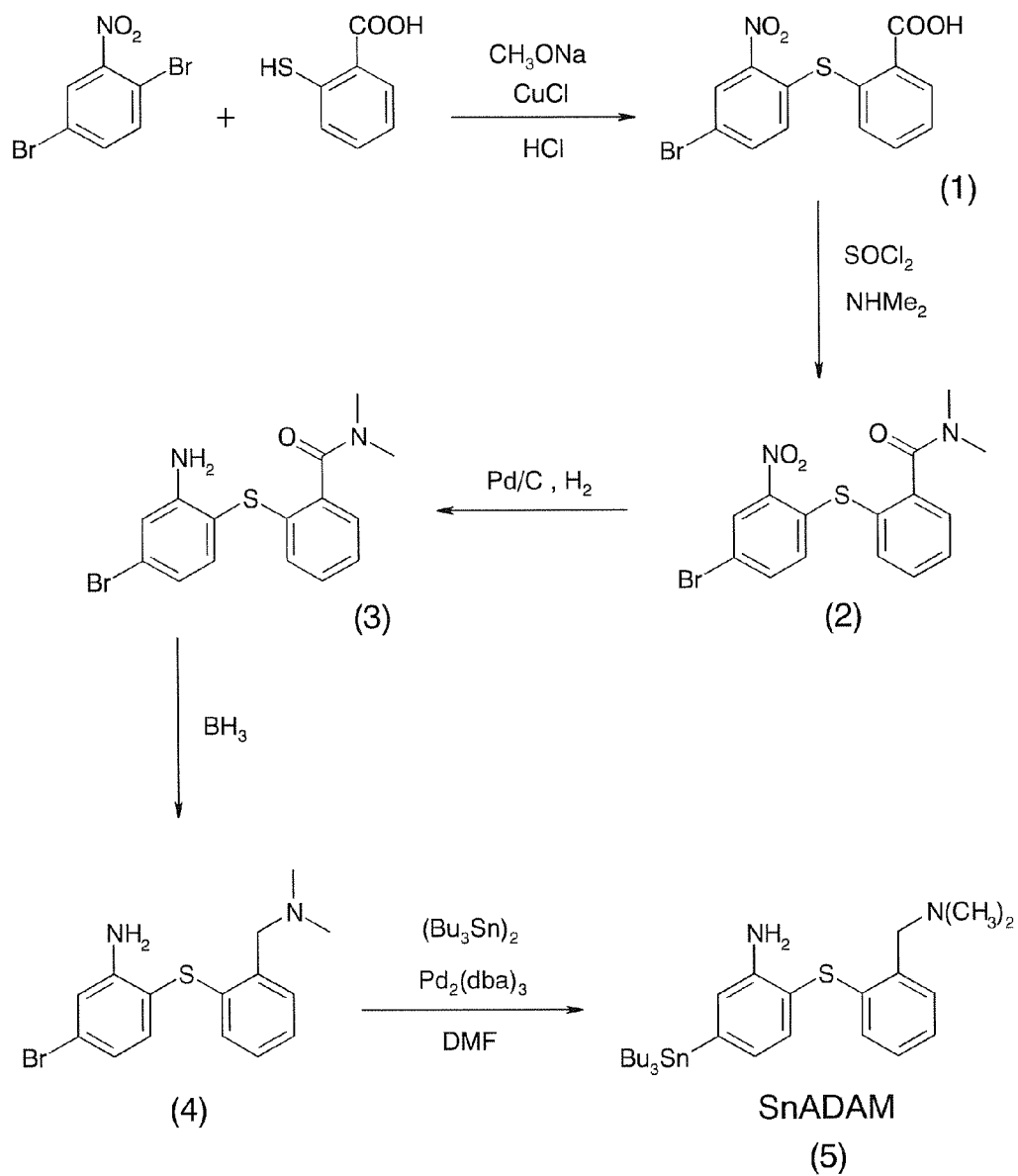
FIG. 4 shows chemical reactions for synthesis of SnADAM of an embodiment according to the present invention.

Refer to FIG. 3 and FIG. 4, a method for preparing a radiotracer precursor SnADAM according to the present invention includes following steps.

Step S1: activate 2-[(4-bromo-2-nitrophenyl)thio]benzoic acid (compound 1) by using thionyl chloride ($SOCl_2$) first and then produce N,N-Dimethyl-2-[(4-bromo-2-nitrophenyl)thio]-benzamide (compound 2) by an amidation reaction between activated compound 1 and dimethylamine.

Step S2: produce [2-((2-amino-4-bromo-phenyl)thio)benzyl]dimethylacetamide (compound 3) through catalyzing and reducing compound 2 with using palladium carbon catalyst and hydrogen gas;

Step S3: produce N,N-dimethyl-2[(4-bromo-2-nitrophenyl)thio]dimethylamine (compound 4) through reducing compound 3 with borane; and Step S4: add compound 4 for carrying out substitution reaction and use tris(dibenzylidene-acetone)dipalladium(0) as a catalyst so as to produce [2-((2-Amino-4-tri-n-butyltinphenyl)-thio)benzyl]-dimethylamine (compound 5), which is a radiotracer precursor, SnADAM.

The method of the present invention not only simplifies the manufacturing processes but also shortens the reaction time. By improving influence and impact of low yield rate of respective step of the manufacturing processes, the yield rate of the final product-SnADAM is increased. Moreover, reaction conditions for the substitution reaction at the catalyst level are also changed. Thereby commercial applications of the radiotracer precursor SnADAM have been developed.

The reaction starts with the compound 1 which is prepared by chemical reactions of a method shown in FIG. 4. Use thiosalicylic acid and 2,5-dibromonitrobenzene as reactants and add sodium methoxide(MeONa) to enhance the reaction for synthesis of sulfide.

In the past, a certain amount of sodium is weighted and cut into thin slices first. The sodium thin slices are put into methanol one by one, and dissolved completely. Then add thiosalicylic acid into the solution and stir the mixture evenly. The solution is concentrated under reduced pressure. Remove the solvent completely by vacuum evaporation at 40° C. At last, add anhydrous tetrahydrofuran (THF) solution and other substanes, such as CuCl and 2,5-dibromonitrobenzene. The solution is heated to reflux for synthesis reaction of sulfide. However, the disadvantage of this method is that the sodium is easy to react with water in the air so that the amount of the sodium required is unable to be weighted precisely. After being cut into slices, the sodium is easier to be oxidized into sodium hydroxide due to increasing area in contact with air. This causes difficulties in quantification. Moreover, in conventional process, sodium slices are added into methanol solution to produce sodium methoxide ($CH_3ONa$). Then the methanol solution is removed by vacuum evaporation. This is not as efficient as adding $CH_3ONa$ directly. Both the reaction processes and reaction time are simplified.

The step S2 features on that the compound 2 is reduced by using Pd/C catalyst and hydrogen gas simultaneously. Thus the product reduced is compound 3 with high purity and no special purification processes are required. Refer to FIG. 2A to FIG. 2D, a mixture of compound 2, compound 3, compound 3A and compound 4 is produced due to incomplete reduction. The present invention saves cost and time required for isolation and purification of the compounds.

Then in the step S3, an amide carbonyl group of the compound 3 is reduced by borane. After being treated by acid and alkali such as hydrochloric acid sodium carbonate, etc., liquid chromatography ($SiO_2$, $CHCl_3$) is used for isolation and purification to get an oily product-compound 4. The yield rate of the compound 4 is table and around 90%. Compared with the maximum yield rate, about 50%, of the conventional borane-cobalt dichloride ($BH_3$—$CoCl_2$) reduction system, the present invention not only dramatically increases the yield rate but also has better reproducibility. Thus the method can be applied to the production line.

The step S4 features on that tris (dibenzylidene-acetone) dipalladium(0) ($Pd_2(dba)_3$) is used as a catalyst and in combination with a nitrogen gas balloon for purge to shorten the reaction/reflux time into 48 hours. The reaction time required is only half of the time the step takes before. This enables SnADAM more likely to be applied commercially.

The followings are data controlled during operation of the present invention and related details.

Synthesis of Compound 1:

Put 4.4 g (77.8 mmol) sodium methoxide (MeONa), 6.0 g (38.9 mmol) thiosalicylic acid, 3.08 g (38.9 mmol) cuprous chloride (CuCl) and 10.9 g (38.9 mmol) 2,5-dibromonitrobenzene into a 100 ml round-bottom flask and then add 50 mL anhydrous tetrahydrofuran(THF) into the mixture. Next the solution is heated to reflux for 24 hours. After the solution being cooled down to room temperature, filter the solution to get filtrate. The filtrate is concentrated by vacuum evaporation at 40° C. Dissolve the sample with 2N hydrochloric acid (HCl) (50 mL) and extract twice with chloroform (50 mL each). Mix the the chloroform extract, remove water by anhydrous sodium sulfate ($Na_2SO_4$) and concentrate the solution by vacuum evaporation at 40° C. The residues after concentration are treated by liquid chromatography ($SiO_2$, $CHCl_3$:$CH_3OH$=9:1) for isolation and purification to get yellow solid product-compound 1 (7.95 g, 57.7%).

Analysis of Compound 1:

IR(KBr) ν 1680 (CO), 1533 and 1347 ($NO_2$) $cm^{-1}$.

$^1H$ NMR ($CD_3OD$) δ 8.29 (d, J=2.4 Hz, 1H), 7.95 (m, 1H), 7.62 (dd, J=8.7 and 2.1 Hz, 1H), 7.56-7.46 (m, 3H), 6.99 (d, J=8.4 Hz, 1H).

MS m/z 355 and 353 ($M^+$), 309 and 307 ($M^+$-$NO_2$)

Synthesis of Compound 2:

Take and put 7.95 g (22.4 mmol) compound 1 and 60 mL thionyl chloride ($SOCl_2$) into a 250 ml round-bottom flask and heat the solution to reflux at 90° C. for 2 hours. After vacuum evaporation at 50° C., dissolve residue in 100 mL chloroform and add 5.5 mL dimethylamine (40% aqueous solution) to the solution in an ice bath. Stir the solution at room temperature for 3 hours and extract twice with with 2N hydrochloric acid (HCl) (100 mL each) and take the lower organic layer. Then remove water by anhydrous sodium sulfate ($Na_2SO_4$) and remove the solvent by vacuum evaporation at 40° C. Use liquid chromatography ($SiO_2$, 100% $CHCl_3$) for isolation and purification to get yellow solid product-compound 2 (7.86 g, 92%).

Analysis of Compound 2:

IR (KBr) ν 1637 (CO), 1517 and 1335 (NO$_2$) cm$^{-1}$.

$^1$H NMR (CDCl$_3$) δ 8.23 (d, J=2.1 Hz, 1H, Ph), 7.53 (m, 2H, Ph), 7.35 (m, 3H, Ph), 6.74 (d, J=8.7 Hz, 1H, Ph), 2.96 (s, 3H, CH$_3$), 2.78 (s, 3H, CH$_3$).

$^{13}$C NMR (CDCl$_3$) δ 168.87 (CO), 145.19, 143.42, 137.13, 137.06, 136.30, 131.02, 130.87, 130.29, 127.95, 127.54, 126.84 and 118.19 (Ph), 38.43 (CH$_3$), 34.47 (CH$_3$).

MS m/z 382 and 380 (M$^+$), 336 and 334 (M$^+$-NO$_2$), 292 and 290 (M$^+$-NO$_2$-N(CH$_3$)$_2$), 264 and 262 (M$^+$-NO$_2$—CON(CH$_3$)$_2$).

Synthesis of compound 4:

Dissolve 4.34 g (11.4 mmol) compound 2 in 80 ml methanol (MeOH). Set the solution in a 100 ml round-bottom flask and add 0.8 g 10% Pd/C catalyst into the flask. Then the solution is poured into a 170 ml reaction vessel for hydrogen reduction reaction with 55 psi of hydrogen and reacted overnight. Filter the solution with diatomaceous earth-(Celite)-545 and take the filtrate. Pour the tiltrate into a 500 ml round-bottom flask and concentrate the filtrate by vacuum evaporation at 40° C. Then the filtrate is concentrated under vacuum at 55° C. for 2 hours to get an intermediate product-compound 3. Add 60 ml anyhydrous tetrahydrofuran and 120 mL (120 mmol) 1.0 M borane-tetrahydrofuran complex into the flask and heat to reflux at 73° C. for 24 hours (with a drying tube). After being cooled down, slowly drop 1N hydrochloric acid into the solution until no bubbles come out. Then concentrate the solution by vacuum evaporation at 30° C., add 120 mL 1N hydrochloric acid into the solution and heat the solution to 80-90° C. for 1 hour. After being cooled down to room temperature, adjust pH value of the solution to 10 with saturated aqueous solution of sodium carbonate (Na$_2$CO$_3$). Extract the solution twice and each with 100 mL of chloroform. The lower organic layer is dehydrated with anhydrous sodium sulfate and dried by vacuum evaporation at 40° C. At last, use liquid chromatography (SiO$_2$, 100% CHCl$_3$) for isolation and purification to get an oily product-compound 4 (3.46 g, 90%).

Analysis of Compound 4:

IR (neat) ν 3458 and 3371 (NH$_2$) cm$^{-1}$.

$^1$H NMR (CDCl$_3$): δ 7.31 (d, J=7.8 Hz, 1H, Ph), 7.22 (m, 1H, Ph), 7.09 (m, 2H, Ph), 6.91 (m, 1H, Ph), 6.82 (m, 2H, Ph), 4.70 (br, 2H, NH$_2$), 3.56 (s, 2H, CH$_2$), 2.29 (s, 6H, CH$_3$).

$^{13}$C NMR (CDCl3) δ 150.14, 138.58, 137.01, 136.53, 130.38, 128.12, 128.07, 125.61, 124.66, 120.94, 117.62 and 114.57 (Ph), 62.49 (CH$_2$), 45.19 (CH$_3$).

MS m/z 338 and 336 (M$^+$), 293 and 291 (M$^+$-N(CH$_3$)$_2$-1).

Synthesis of SnADAM, Compound 5:

Put 3.46 g (10.3 mmole) compound 4 and 0.282 mg (0.3 mmol) tris(dibenzylideneacetone)dipalladium(0) (Pd$_2$(dba)$_3$) in a 250 ml two-neck round-bottom flask. Run a pump to create vacuum for 2 hours and pruge with nitrogen gas. 10 ml anhydrous dimethylformamide (DMF) is added into the flask after 20.1 mL (36.1 mmole) and 90 ml anhydrous tetrahydrofuran being added into the flask. After being released from the purge with nitrogen gas and attached with a nitrogen gas balloon, heat the flask to 73° C. and react for 48 hours. After the reaction being completed, filter the solution with diatomaceous earth and wash the solution with chloroform. Collect the filtrate and remove the solvent by vacuum evaporation. Next liquid chromatography (SiO$_2$) is carried out. Impurities with low polarity are first eluted from the column by using 100% n-hexane. Then use 100% chloroform for isolation and purification to get the final product-compound 5, the radiotracer precursor SnADAM (2.82 g, 50%).

Analysis of Compound 5:

IR (neat) ν 3465 and 3375 (NH$_2$) cm$^{-1}$.

$^1$H NMR (CDCl$_3$) δ 7.40 (d, J=7.2 Hz, 1H, Ph), 7.25 (m, 1H, Ph), 7.08 (m, 2H, Ph), 6.91 (m, 1H, Ph), 6.82 (m, 2H, Ph), 4.41 (br, 2H, NH$_2$), 3.58 (s, 2H, CH$_2$), 2.31 (s, 6H, NCH$_3$), 1.53 (m, 6H, Bu), 1.35 (m, 6H, Bu), 1.06 (m, 6H, Bu), 0.90 (t, J=7.3 Hz, 9H, Bu).

$^{13}$C NMR (CDCl$_3$) δ 148.08, 145.29, 137.18, 136.71, 136.28, 130.06, 127.80, 127.62, 126.33, 125.11, 123.08 and 115.20 (Ph), 62.26 (NCH$_2$), 45.23 (NCH$_3$), 29.04, 27.32 and 9.55 (CH$_2$CH$_2$CH$_2$CH$_3$), 13.63 (CH$_2$CH$_3$).

MS m/z 548 and 546 (M$^+$), 491 and 489 (M$^+$-CH$_2$N(CH$_3$)$_2$+1)

In summary, the present invention provides a method for preparing a radiotracer precursor SnADAM that overcomes shortcomings of conventional methods including lower yield rate and time-consuming. The reduction reaction is modified for avoiding the generation of a large amount of intermediate products with similar structures so that there is no need to perform isolation and purification processes. Moreover, the yield rate of the intermediate products is also increased so that its impact on the low yield rate of the final product SnADAM is reduced. Furthermore, the catalyst used has been changed so as to significantly accelerate a part of the reactions. In conclusion, the manufacturing processes of the present invention are modified to ensure a successful implementation and shorten production time (3 days less than before). Therefore the method of the present invention for preparing the radiotracer precursor SnADAM is of economic value.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

The invention claimed is:

1. A method for preparing a radiotracer precursor SnADAM comprising the steps of:

activating 2-[(4-bromo-2-nitrophenyl)thio]benzoic acid by thionyl chloride (SOCl$_2$) and producing N,N-Dimethyl-2[(4-bromo-2-nitrophenyl)thio]-benzamide by an amidation reaction between 2-[(4-bromo-2-nitrophenyl)thio]benzoic acid activated and dimethylamine;

catalyzing and reducing N,N-Dimethyl-2-[(4-bromo-2-nitrophenyl)thio]-benzamide by using palladium carbon catalyst and hydrogen gas and thus [2-((2-amino-4-bromo-phenyl)thio)benzyl]dimethylacetamide is produced;

reducing [2-((2-amino-4-bromo-phenyl)thio)benzyl]dimethylacetamide by borane to produce N,N-dimethyl-2-[(4-bromo-2-nitrophenyl)thio]-dimethylamine; and adding bis(tri-n-butyltin) into N,N-dimethyl-2-[(4-bromo-2-nitrophenyl)thio]-dimethylamine for carrying out substitution reaction and using tris(dibenzylidene-acetone)dipalladium(0) as a catalyst so as to produce [2-((2-Amino-4-tri-n-butyltinphenyl)thio)benzyl]-dimethylamine, which is a radiotracer precursor, SnADAM.

2. The method as claimed in claim 1, wherein in the step of activating 2-[(4-bromo-2-nitrophenyl)thio]benzoic acid by thionyl chloride, thiosalicylic acid and 2,5-dibromonitrobenzene are reactants while sodium methoxide (MeONa) is added directly to enhance efficiency of a reaction for synthesis of sulfide so as to produce 2-[(4-bromo-2-nitrophenyl)thio]benzoic acid.

3. The method as claimed in claim 2, wherein in the reaction for synthesis of sulfide, cuprous chloride is added.

4. The method as claimed in claim 1, wherein the step of reducing [2-((2-amino-4-bromo-phenyl)thio)benzyl]dimethylacetamide by borane further includes a step of adding hydrochloric acid and saturated aqueous solution of sodium carbonate ($Na_2CO_3$) in turn.

5. The method as claimed in claim 4, wherein in the step of adding hydrochloric acid and saturated aqueous solution of sodium carbonate ($Na_2CO_3$) in turn, heat a solution up to 80-90° C. for 1 hour and then cool down the solution to room temperature before adding saturated aqueous solution of sodium carbonate.

6. The method as claimed in claim 1, wherein the step of adding bis(tri-n-butyltin) into N,N-dimethyl-2-[(4-bromo-2-nitrophenyl)thio]-dimethylamine for carrying out substitution reaction further includes a step of purging with nitrogen gas.

* * * * *